Figure 1:
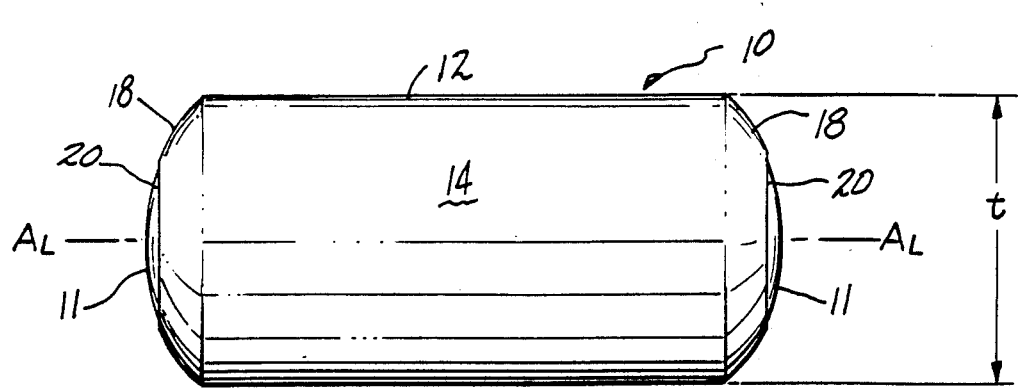
Figure 2:
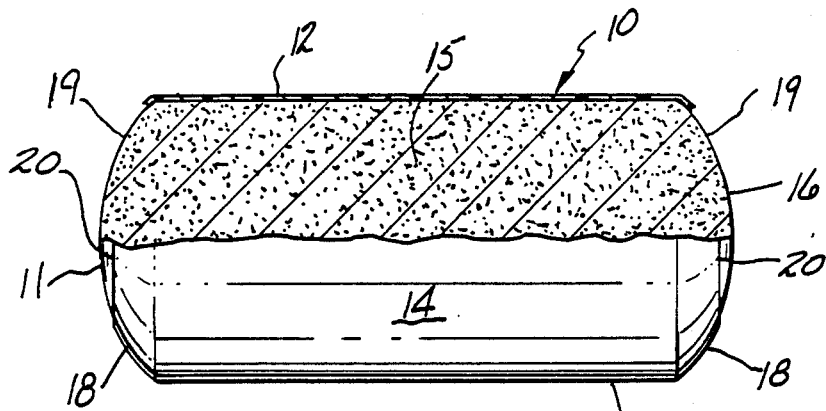
Figure 3:
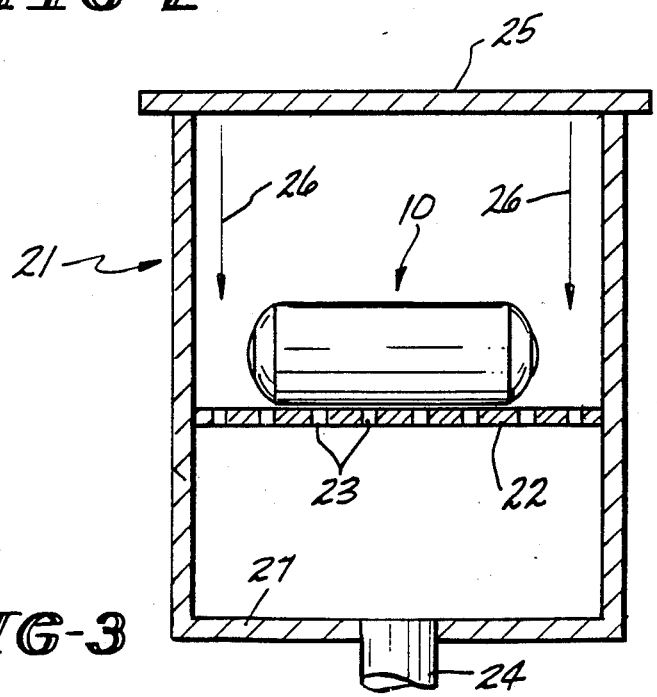
Figure 4:
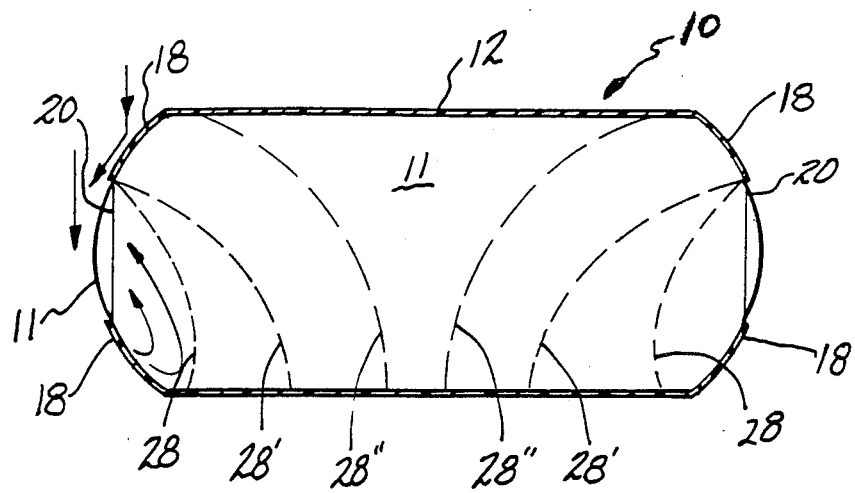
Figure 6:
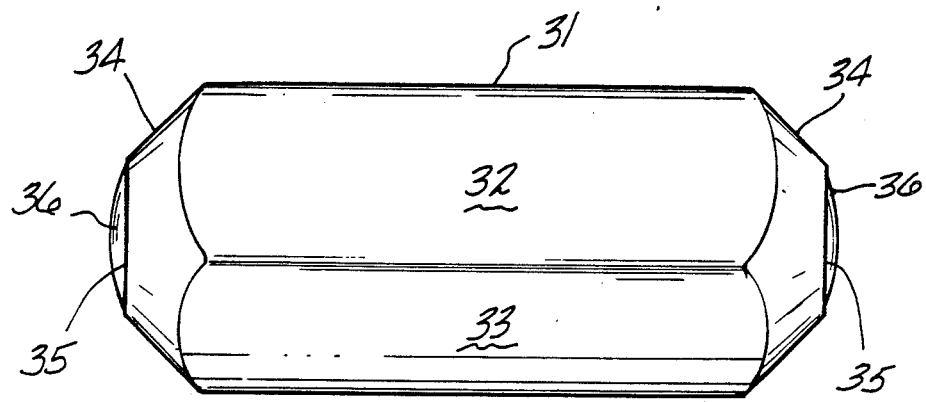

United States Patent [19]

Legros

[11] Patent Number: 4,923,619
[45] Date of Patent: May 8, 1990

[54] DISINFECTANT COMPOSITIONS AND DISINFECTION PROCESS APPLICABLE TO INFECTED LIQUIDS OR SURFACES

[75] Inventor: Alain C. A. G. Legros, Nalinnes, Belgium

[73] Assignee: Fabricom Air Conditioning S.A., Nalinnes, Belgium

[21] Appl. No.: 73,796

[22] PCT Filed: Oct. 14, 1986

[86] PCT No.: PCT/BE86/00032
§ 371 Date: Aug. 3, 1987
§ 102(e) Date: Aug. 3, 1987

[87] PCT Pub. No.: WO87/02221
PCT Pub. Date: Apr. 23, 1987

[30] Foreign Application Priority Data

Oct. 17, 1985 [LU] Luxembourg ............ 86.123

[51] Int. Cl.$^5$ ............................................. C02F 1/68
[52] U.S. Cl. .................................... 210/764; 422/28; 422/29; 422/32
[58] Field of Search ................... 422/28, 29, 32; 210/764

[56] References Cited

U.S. PATENT DOCUMENTS

| | | |
|---|---|---|
| 2,271,378 | 1/1942 | Searle . |
| 3,681,492 | 9/1972 | Kotzbauer .................. 210/764 |
| 3,702,298 | 11/1972 | Zsoldus et al. ............. 210/764 |
| 3,928,323 | 12/1975 | Green et al. . |
| 3,928,923 | 12/1975 | Harte . |
| 3,933,812 | 1/1976 | Green et al. . |
| 3,961,042 | 6/1976 | Green et al. .............. 210/764 |
| 3,966,904 | 6/1976 | Green et al. .............. 210/764 |
| 4,010,252 | 3/1977 | Hewitt ....................... 424/47 |
| 4,025,617 | 5/1977 | Green et al. . |
| 4,025,627 | 5/1977 | Green et al. . |
| 4,026,945 | 5/1977 | Green et al. . |
| 4,035,480 | 7/1977 | Green et al. . |
| 4,043,932 | 9/1977 | Fresenius et al. .......... 210/764 |
| 4,073,924 | 2/1978 | Sonntag ..................... 210/764 |
| 4,073,926 | 2/1978 | Sonntag et al. ............ 210/764 |
| 4,073,927 | 2/1978 | Freilich ..................... 210/764 |
| 4,098,602 | 7/1978 | Seymour et al. .......... 71/67 |
| 4,217,914 | 8/1980 | Jacquet et al. . |
| 4,492,618 | 1/1985 | Eder .......................... 210/764 |
| 4,719,083 | 1/1988 | Baker ........................ 210/764 |

FOREIGN PATENT DOCUMENTS

| | | |
|---|---|---|
| 0059978 | 9/1982 | European Pat. Off. . |
| 2235539 | 2/1974 | Fed. Rep. of Germany . |
| 2530487 | 1/1977 | Fed. Rep. of Germany . |
| 2911288 | 2/1980 | Fed. Rep. of Germany . |
| 2143449 | 6/1972 | France . |
| 2355512 | 6/1977 | France . |

Primary Examiner—David L. Lacey
Assistant Examiner—Lori-Ann Johnson
Attorney, Agent, or Firm—Sughrue, Mion, Zinn, Macpeak & Seas

[57] ABSTRACT

Disinfectant composition and disinfection process for infected liquids or surfaces using, in addition to ions of at least one metal selected among copper, silver and manganese, a quaternary ammonium polymer or copolymer obtained by condensation of at least one difunctional tertiary amine with an organic halide.

10 Claims, No Drawings

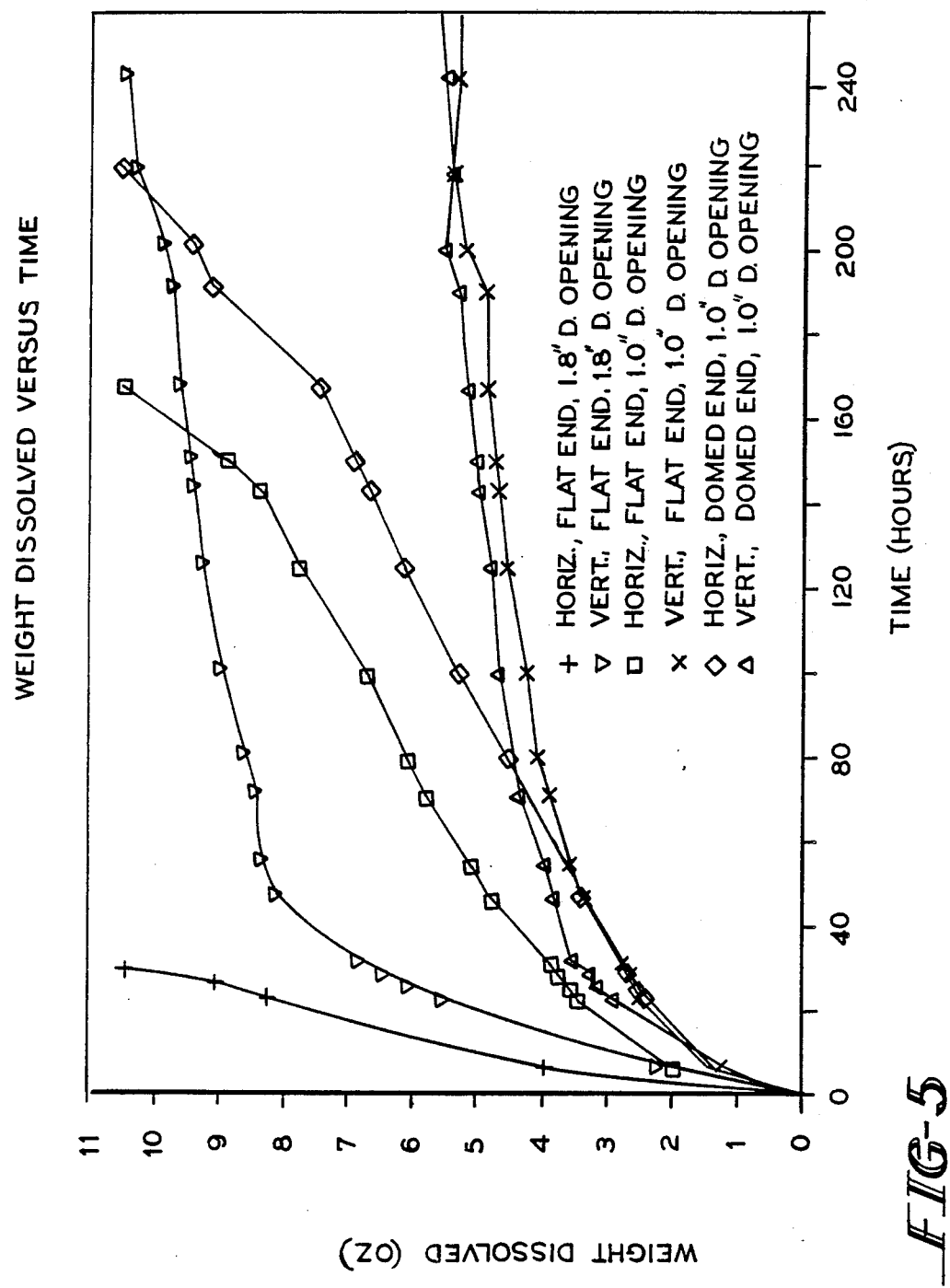

DISINFECTANT COMPOSITIONS AND DISINFECTION PROCESS APPLICABLE TO INFECTED LIQUIDS OR SURFACES

This invention relates to disinfectant compositions and to a method of disinfection for liquids or infected surfaces.

The compositions and method according to the invention are particularly usable for disinfecting liquids such as waters or cutting oils. They are also usable for infected surfaces, such as surfaces of industrial or hospital installations, in particular, tanks, pipes and tubes, . . . of the food industry, more particularly of the breweries, dairies, . . .

In the case of the use of the disinfectant composition in the food industry such as defined hereabove, the composition may also be associated, without any loss of effectiveness, to a cleaning product such as a surfactant, preferably of the non-ionic type.

In a particular application, the compositions and the process according to the invention are usable, on the one hand, for treating water which must or may be recycled such as, for example, water of swimming pools and, on the other hand, for treating residual waters and even effluents which must or may not be recycled and which are used, for example, in air conditioning, in domestic water, drink water, etc.

It is known to disinfect, i.e. to eliminate bacterial germs from water of swimming pools, by using halogens, in particular chlorine or bromine. However, the use of these products has disadvantages, such as the apparition of offensive smell, the irritation of some mucous membranes and even the formation of halogenous compounds having a cancerogenic action.

It is also known to use peroxide compounds such as hydrogen peroxide or persulphate of sodium or potassium in order to remove bacterial germs from the water of swimming pools. In the same way, the removal of algae and germs may also be effected by treating water with copper or/and silver ions.

The simultaneous use of peroxide compounds and copper and/or silver ions, as well as the use of ammonium quaternary compounds and hydrogen peroxide, have also been proposed (see German patents DE-A-22 35 539, 25 30 487 and 29 11 288).

Finally, the treatment of water of swimming pools and of industrial water by means of a combination (a) of ammonium quaternary compounds, (b) of water-soluble copper and/or silver salts and (c) of peroxide compounds releasing oxygen such as monopersulphate or peroxidisulphate of potassium is known.

Applicant has found that the simultaneous use of an ammonium quaternary polymer and also of very small amounts of copper and/or silver and/or manganese ions allows to disinfect water, cutting oils and infected surfaces in a very short time without using at the same time a peroxide compound.

In particular, Applicant has discovered a clearly synergistic effect by using simultaneously at least one ammonium quaternary polymer or copolymer and copper and/or silver and/or manganese ions instead of using the ammonium polymer or copolymer alone, copper ions alone, silver ions alone or manganese ions alone.

The present invention thus relates to a disinfectant composition containing, as active ingredients, at least one ammonium quaternary polymer and ions of metals selected among copper, silver and manganese, this disinfectant composition being essentially characterized in that it contains as ammonium quaternary polymer at least one polymer or copolymer obtained by condensation of at least one difunctional tertiary amine having one of the following formulae (I), (II) and (III):

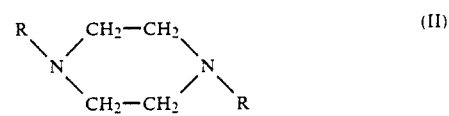

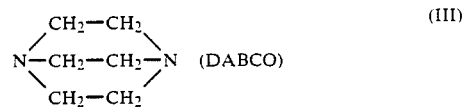

with at least one organic dihalide having the following formula (IV):

$$X-B-X \quad (IV)$$

in which formulae (I), (II), (III) and (IV), the symbols R, A, B and X have the following meanings:

R designates a lower alkyl radical or the radical $-CH_2-CH_2-OH$;

X designates a halogen atom, preferably a chlorine or bromine atom, and

A and B, which may be identical or different, have one of the five following formulae:

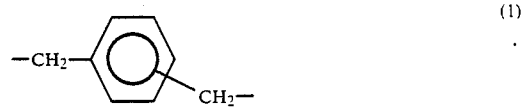

in which one of the substituents $-CH_2$ may be in an ortho, meta or para position, .

where D designates hydrogen or an alkyl radical containing less than four carbon atoms, and x and y are integers lower than 5, one of which may have a value equal to 0, while the sum $x+y$ is at least equal to 1 and at most equal to 10, the radical (2) containing at most two double bonds,

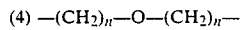

in which n is equal to 2 or 3, and

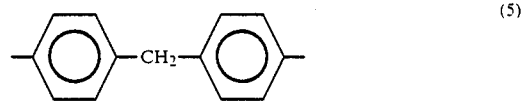

The invention relates also to a process of disinfection consisting essentially in treating a liquid or an infected surface with ions of a metal selected among copper, silver and manganese, as also with at least one ammonium quaternary polymer or copolymer of the type defined hereabove.

According to a first embodiment of the compositions or the process according to the invention, the ammonium quaternary polymer used is a polymer of the following formula (V):

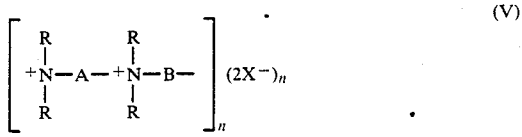

in which R, A, B and X have the above meanings, while n designates the degree of polymerization.

In a second embodiment of the compositions and of the process according to the invention, the ammonium quaternary polymer used has the following formula (VI):

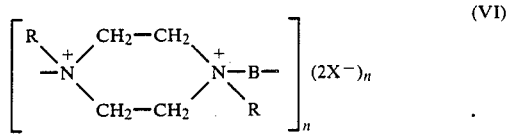

in which R, X, B and n have the above meanings.

In a third embodiment of the compositions and the process according to the invention, an ammonium quaternary polymer of the following formula (VII) is used:

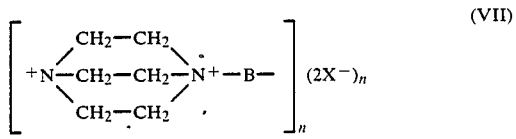

in which B, X and n have the above meanings.

The ammonium quaternary polymers of formula (V) obtained by condensation of a diamine of formula (I) with a dihalide of formula (IV) are known compounds, the synthesis and the use of which in cosmetic compositions, namely for the treatment of hair and of the skin, are described in the U.S. Pat. No. 4,217,914.

Moreover, the U.S. Pat. No. 4,035,480 describes the preparation and use, as bactericidal agents, of mixtures of ammonium quaternary polymers obtained by condensation of a 1,4-dihalo-2-butene, particularly the 1,4-dichloro-2-butene, with a heterocyclic difunctional tertiary amine of formula (II) in which the R symbols designate each a methyl radical.

Some polymers of formula (VII) formed by condensation of the diamine of formula (III) with an organic dihalide of formula (IV) are known compounds of which the preparation and the microbicidal properties are described in the U.S. Pat. Nos. 4,025,627 and 4,035,480 and in a publication of Salomone J. C. and Snider B., Journal of Polymer Science, Part A-1, vol 8, pages 3495 to 3501, 1970.

Some copolymers obtained by condensation of trifunctional tertiary diamines according to one of the formulae (I), (II) and (III) with an organic dihalide of formula (IV) are described in the U.S. Pat. Nos. 3,933,812, 3,928,323, 4,025,617 and 4,026,945 which describe the bactericidal properties of these copolymers.

The simultaneous use, according to the present invention, of at least one ammonium quaternary polymer or copolymer formed by condensation of a difunctional tertiary amine of formulae (I), (II) or (III) with an organic dihalide of formula (IV) and of at least one ion selected among the copper, silver and manganese ions, gives unexpected effects on the speed of destruction of numerous microorganisms.

In fact, Applicant has discovered that copper, silver and/or manganese ions potentiate remarkably the destruction of microorganisms by means of the above cited ammonium quaternary polymers or copolymers.

This unexpected effect of synergy will be demonstrated in the following description.

The ammonium quaternary polymers and copolymers used in the examples I to XXI given hereafter in order to demonstrate the remarkable bactericidal effects of these polymers and copolymers, when they are used together with copper, silver and/or manganese ions, have been synthesized by the general method described hereafter:

Stoichiometric quantities (1 mole per liter) of a tertiary diamine of formula (I), (II) and/or (III) and of an organic dihalide of formula (IV) have been stirred at room temperature in a solvent consisting of 80% by volume of dimethylformamide and of 20% by volume of water. When several diamines of formula (I), (II) and/or (III) have been used, the sum of their concentrations was also of one mole per liter.

After a determined reaction time, the obtained polymer and/or copolymer was precipitated by adding anhydrous acetone and the precipitate was finally filtered and dried.

The percentage by weight of halide ions in the polymer and/or copolymer obtained by the reaction of condensation was determined by titration by means of silver nitrate in the presence of sodium chromate, as indicator of the end of titration.

The yield of the polymerization and/or copolymerization was calculated by means of the following formula:

$$\eta = \frac{\text{weight of recovered polymer or copolymer}}{\text{total weight of the reagents}}$$

The possible modifications in this general method are given in the different examples of synthesis given hereafter.

PREPARATION OF AMMONIUM QUATERNARY POLYMERS AND COPOLYMERS OF ONE OF THE FORMULAE (V), (VI) AND (VII)

EXAMPLE 1

Preparation of a polymer of formula (VII) in which B=CH$_2$—CH$_2$—CH$_2$ and X=Br 27.9 g of the DABCO product of formula (III) and 50 g of 1,3-dibromo-propane were stirred during 216 hours at 25° C. in 600 ml of anhydrous methanol. The yield of the reaction was of 32% and the polymer contained 43.21% of bromide.

EXAMPLE 2

Preparation of a polymer of formula (V) in which
R=—CH$_3$, A=—CH$_2$—CH$_2$—,

B = —CH$_2$— 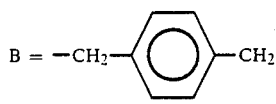 —CH$_2$ and X=Br 22 g de N,N,N',N'-tetramethylethane diamine and 50 g of p-xylylidene bromide were reflux heated during 50 hours in 600 ml of anhydrous methanol. The reaction mixture was then maintained at 20° C. during 40 hours. The yield of the reaction was of 72% and the polymer contained 38.5% of bromide.

EXAMPLE 3

Preparation of a polymer of formula (VI) in which
R=—CH$_3$, B=—CH$_2$—CH=CH—CH$_2$— and X=Br 26.7 g of N,N'-methylpiperazine and 50 g of 1,4-dibromo-2-butene were reflux heated during one hour in 600 ml of anhydrous methanol. The yield of the reaction was of 94% and the polymer contained 47.26% of bromide.

EXAMPLE 4

Preparation of a polymer of formula (VII) in which

B = —CH$_2$—CH—CH$_2$—
         |
         OH

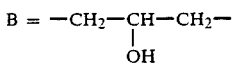

and X=Br 25.7 g of the DABCO product of formula (III) and 50 g of 1,3-dibromo-2-propanol were reflux heated during 52 hours in 600 ml of a mixture containing 50% of methanol and 50% of dimethylformamide. The yield of the reaction was of 48% and the polymer contained 38.73% of bromide.

EXAMPLE 5

Preparation of a polymer of formula (VII) in which
B=—CH$_2$—CH$_2$—CH$_2$—CH$_2$—CH$_2$— and X=Br 24.4 g of the DABCO product of formula (III) and 50 g of 1,5-dibromo-pentane were reflux heated during 82 hours in 600 ml of methanol. The yield of the reaction was of 80% and the polymer contained 41.7% of bromide.

EXAMPLE 6

Preparation of a polymer of formula (VII) in which
B=—CH$_2$—CH$_2$—CH$_2$—CH$_2$— and X=Br 26 g of the DABCO product of formula (III) and 50 g of 1,4-dibromo-butane were reflux heated during 41 hours in 600 ml of anhydrous methanol. The yield of the reaction was of 55% and the polymer contained 43.01 of bromide.

EXAMPLE 7

Preparation of a polymer of formula (VII) in which
B=—CH$_2$—CH=CH—CH$_2$— and X=Br 26.2 g of DABCO product of formula (III) and 50 g of 1,4-dibromo-2-butene were reflux heated during 1 hour in 600 ml of anhydrous methanol. The yield of the reaction was of 99% and the polymer contained 41.18% of bromide.

EXAMPLE 8

Preparation of a polymer of formula (VII) in which
B=—CH$_2$—CH$_2$—O—CH$_2$—CH$_2$— and X=Br 24.2 g of the DABCO product of formula (III) and 50 g of 1,5-dibromo-diethylether were stirred during 432 hours at 20° C. in 600 ml of a mixture containing 50% of anhydrous methanol and 50% of dimethylformamide. The yield of the reaction was of 63% and the polymer contained 38.94% of bromide.

EXAMPLE 9

Preparation of a polymer of formula (VII) in which
B=—CH$_2$—CH$_2$—CH$_2$— and X=Br 38.8 g of the DABCO product of formula (III) and 70 g of 1,3-dibromo-propane were reacted during 110 hours at 25° C. in 500 ml of a mixture containing 80% of dimethtylformamide and 20% of water. The yield of the reaction was of 87% and the polymer contained 43.62% of bromide.

EXAMPLE 10

Preparation of a polymer of formula (V) in which
R=—CH$_3$,
A=—CH$_2$—CH$_2$—CH$_2$—CH$_2$—CH$_2$—CH$_2$—;
B=—CH$_2$—CH$_2$—CH$_2$— and X=Br 86.15 g of N,N,N',N'-tetramethylhexane diamine and 100.95 g of 1,3-dibromo-propane were reacted during 205 hours at 25° C. in 550 ml of a mixture containing 80% of dimethylformamide and 20% of water. The yield of the reaction was greater than 72% and the polymer contained 41.76% of bromide.

EXAMPLE 11

Preparation of a polymer of formula (V) in which
R=—CH$_3$,
A=—CH$_2$—CH$_2$—CH$_2$—CH$_2$—CH$_2$—CH$_2$—,
B=—CH$_2$—CH$_2$—CH$_2$— and X=Br 172.3 g* of N,N,N',N'-tetramethylhexane diamine and 201.9 g* of 1,3-dibromo-propane were reacted during 182 hours at 25° C. in 550 ml of a mixture* containing 80% of dimethylformamide and 20% of water. After this reaction, the polymer was precipitated by means of anhydrous acetone. The yield of the reaction was of 80% and the polymer contained 41.37% of bromide (*i.e. 2 molar solution for each reagent).

EXAMPLE 12

Preparation of a polymer of formula (V) in which
R=—CH$_3$,
A=—CH$_2$—CH$_2$—CH$_2$—CH$_2$—CH$_2$—CH$_2$—,
B=—CH$_2$—CH$_2$—CH$_2$— and X=Br 25.6 g of N,N,N',N'-tetramethylhexane diamine and 30 g of 1,3-dibromo-propane were reacted during 48 hours at the reflux temperature in 500 ml of anhydrous methanol. After this reaction, a polymer containing 40.07% of bromide was recovered. This polymer was introduced into 300 ml of water and the mixture was reflux heated during 75 hours. A polymer containing 41.57% of bromide was obtained.

EXAMPLE 13

Preparation of a polymer of formula (V) in which
R=—CH$_3$,
A=—CH$_2$—CH$_2$—CH$_2$—CH$_2$—CH$_2$—CH$_2$—,
B=—CH$_2$—CH$_2$—CH$_2$— and X=Br 25.6 g of N,N,N',N'-tetramethylhexane diamine and 30 g of 1,3-dibromo-propane were reacted during 24 hours at the reflux temperature in 500 ml of isopropanol. 50 ml of water were then added to the reaction mixture. The so-obtained composition was reacted at the reflux temperature during 24 hours. A polymer containing 39.96% of bromide was recovered.

EXAMPLES 14 to 20

Preparation of polymers of formula (V) in which R, A, B and X have the meanings given in the table I Table I indicates the conditions for preparing the various polymers, the yield of the reaction η, the content of halide contained in the polymer expressed in % by weight and the reaction time.

TABLE I

| Example No. | Remarks | R | A | B | X | Time of reaction hours | η % | % halide |
|---|---|---|---|---|---|---|---|---|
| 14 | solvent used: dimethyl-formamide | r | c | a | Br | 168 | 85 | 42.19 |
| 15 | addition of 30% of water after 2 h | r | a | d | Br | 168 | 96 | 38.98 |
| 16 | solvent: 50% dimethyl-formamide and 50% of water | r | c | b | Br | 480 | 95 | 39.83 |
| 17 | addition of 30% of water after 2 h | r | b | b | Cl | 312 | 87 | 23.33 |
| 18 | — | r | b | e | Br | 480 | 83 | 40.53 |
| 19 | addition of 30% of water after 2 h | r | c | d | Br | 72 | 89.4 | 35.48 |
| 20 | — | r | b | f | Br | 456 | 93 | 37.86 | r = CH$_3$
a = —CH$_2$—CH$_2$—CH$_2$—
b = —CH$_2$—CH=CH—CH$_2$—
c = —CH$_2$—CH$_2$—CH$_2$—CH$_2$—CH$_2$—CH$_2$—

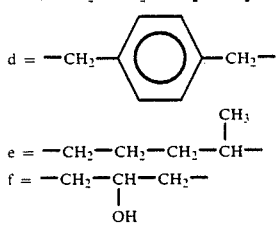

e = —CH$_2$—CH$_2$—CH$_2$—CH—
                              |
                              CH$_3$ f = —CH$_2$—CH—CH$_2$—
              |
              OH

EXAMPLES 21 and 22

Preparation of polymers of formula (VI) in which R, B and X have the meanings given in table II Table II gives the conditions for preparing the various polymers, the yield of the reaction η, the content of halide contained in the polymer expressed in % by weight and the time of reaction.

TABLE II

| Example No. | Remarks | R | B | X | time of reaction hours | η % | % halide |
|---|---|---|---|---|---|---|---|
| 21 | — | r | b | Br | 264 | 99 | 46.18 |
| 22 | solvent: 50% of dimethylformamide and 50% of water | r | d | Br | 72 | 90.4 | 39.13 | r = —CH$_3$
b = —CH$_2$—CH=CH—CH$_2$—

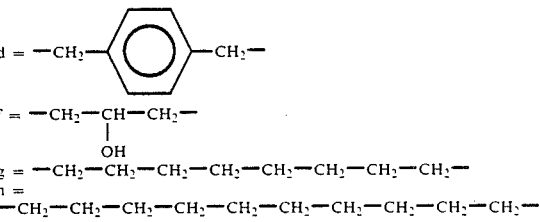

EXAMPLES 23 to 29

Preparation of polymers of formula (VII) in which B and X have the meanings given in table III This table gives also the conditions of preparation of the various polymers, the yield of the reaction η, the content of halide in the polymer expressed in % by weight and the time of reaction.

TABLE III

| Example No. | Remarks | B | X | Time of reaction hours | η % | % halide |
|---|---|---|---|---|---|---|
| 23 | 0.7 molar in reagents | f | Br | 672 | 56 | 39.79 |
| 24 | 0.7 molar in reagents | a | Br | 432 | 91.1 | 38.91 |
| 25 | — | c | Br | 408 | 89.3 | 43.06 |
| 26 | — | g | Br | 408 | 98 | 34.88 |
| 27 | — | h | Br | 410 | 93.1 | 36.36 |
| 28 | — | d | Br | 144 | 99 | 38.77 |
| 29 | — | b | Br | 72 | 100 | 46.44 | a = —CH$_2$—CH$_2$—CH$_2$—
b = —CH$_2$—CH=CH—CH$_2$—
c = —CH$_2$—CH$_2$—CH$_2$—CH$_2$—CH$_2$—CH$_2$—

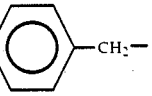

f = —CH$_2$—CH—CH$_2$—
              |
              OH
g = —CH$_2$—CH$_2$—CH$_2$—CH$_2$—CH$_2$—CH$_2$—CH$_2$—CH$_2$—
h = —CH$_2$—CH$_2$—CH$_2$—CH$_2$—CH$_2$—CH$_2$—CH$_2$—CH$_2$—CH$_2$—CH$_2$—

EXAMPLE 30

Preparation of an ammonium quaternary copolymer 28.04 g of the DABCO product of formula (III), 28.55 g of N,N'-dimethylpiperazine and 100.95 g of 1,3-dibromo-propane were added to 500 ml of a mixture containing 80% of dimethylformamide and 20% of water. The reaction mixture was stirred during 360 hours at 25° C. The yield of the reaction was of 83% and the percentage of bromide in the copolymer was of 46.08%.

EXAMPLE 31

Preparation of an ammonium quaternary copolymer 48.83 g of 1,4-dichloro-2-butene, 50 g of N,N,N',N'-tetramethyl-2-butene-1,4 diamine and finally 4.45 g of N,N'-dimethyl-piperazine (drop by drop) were added to 100 ml of water, the mixture of those products being maintained at a temperature comprised between 60° and 70° C.

The mixture was then stirred during one hour at a temperature of 100° C. After cooling the mixture, a yield of the reaction of 96% and a content by weight of chlorine in the copolymer of 24.45% were measured.

EXAMPLE 32

Preparation of an ammonium quaternary copolymer 50 g of N,N,N',N'-tetramethyl-2-butene-1,4 diamine and 39.4 g of the DABCO product of formula (III) were added to 180 g of water. 88 g of 1,4-dichloro-2-butene were added drop by drop to this mixture, the temperature being maintained between 60° and 70° C.

The mixture was then stirred during 1 hour at a temperature of 100° C. After cooling the mixture, a yield of reaction of about 100% and a content by weight of chlorine in the copolymer of 26.04% were measured.

EXAMPLE 33

Preparation of an ammonium quaternary copolymer.

28.04 g of the DABCO product of formula (III), 43.08 g of N,N,N',N'-tetramethylhexane diamine and 115 g of 1,5-dibromopentane were reacted at 25° C. under agitation during 480 hours in 500 ml of a mixture containing 80% of dimethylformamide and 20% of water. The yield of the reaction was of 91% and the percentage of bromide in the copolymer was of 38.42%.

EXAMPLE 34

Preparation of a polymer of formula (VII) in which $$B = -CH_2-\phenyl-CH_2-$$

and X=Br 21.3 g of the DABCO product of formula (III) and 50 g of 1,4-dibromo-p-xylylidene were reacted in 600 ml of a mixture containing 80% of methanol and 20% of water during 24 hours by reflux.

The polymer was crystallized by cooling the reaction mixture and was recovered as indicated in the above described experimental protocol.

The yield of the reaction was of 96% and the percentage by weight of bromide in the polymer was of 36.57%.

EXAMPLE 35

Preparation of a polymer of formula (V) in which
A=—CH₂—CH₂—,
B=—CH₂—CH₂—O—CH₂—CH₂—, R=—CH₃ and
X=Br 50 g of N,N,N',N'-tetramethylethylene diamine and 100 g of 1,5-dibromo-diethylether were reacted during 12 hours at the reflux temperature in 300 ml of a mixture containing 50% of dimethylformamide and 50% of water. The yield of the reaction was of 99% and the polymer contained 41.71% of bromide.

Among the numerous ammonium quaternary polymers and copolymers usable in the disinfectant compositions and in the method according to this invention simultaneously with copper, silver and/or manganese ions, the hexadimethrine bromide of the following formula (II):

$$\left[ -\overset{\overset{CH_3}{|}}{\underset{\underset{CH_3}{|}}{N}}-(CH_2)_6-\overset{\overset{CH_3}{|}}{\underset{\underset{CH_3}{|}}{N}}-(CH_2)_3- \right]_n 2Br^- \quad (II)$$

in which n=14 to 28 may in particular be mentioned. This polymer is known in the cosmetic and pharmacological field, namely as antagonist of heparin.

The disinfectant compositions according to the present invention are preferably in the form of aqueous solutions containing variable amounts of at least one ammonium quaternary polymer of the formula (V), (VI) and/or (VII), or at least one ammonium quaternary copolymer such as defined above as well as copper, silver and/or manganese ions in the form of water-soluble salts of these metals, such as sulfate, chloride, nitrate, etc.

These disinfectant compositions according to the invention are simply added to the liquids to be disinfected or applied onto the surface of the article to be disinfected.

When the composition or the method according to the invention are applied to the disinfection of water, at least one ammonium quaternary polymer (V), (VI), (VII) or one copolymer as defined hereabove is preferably used in the proportion of 0.5 to 1000 parts per million (ppm) of the aqueous medium to be disinfected. In respect of the ions of metals, such as copper and silver, which may be produced within the medium by electrolysis or by addition thereto of water-soluble salts of these metals, such as sulfate, chloride, nitrate, etc., they are preferably used at concentrations of 0.5 to 5 ppm for the copper ions and of 1 to 50 ppb (parts per billion), more particularly of 1 to 10 ppb for the silver ions.

The unexpected synergistic action resulting of the simultaneous use of at least one ammonium quaternary polymer of formula V, VI or VII or of one ammonium quaternary copolymer, as well as copper ions and silver ions is shown in the following comparative tests, based on the destruction speed of various microorganisms selected as non-limiting examples among the microorganisms usually infesting water of swimming pools.

These microorganisms are following:
Escherichia coli ATCC 11229
Pseudomonas aeruginosa ATCC 17934
Staphylococcus aureus ATCC 6538
Streptococcus faecalis ATCC 6569
Saccharomyces cerevisiae
Candida albicans
Lactobacillus.

For making the tests, the well known method of successive dilutions in test tubes and of seeding on a culture medium of tryptone-glucose-extract agar, using a polyphosphate as neutralizing agent was used.

The test of water disinfection of the following examples I to XXVIII were carried out in city supply water having a hardness of about 35° F., said water having previously been filtered on a millipore filter of 0.22μ, after three successive subcultures of each strain of microorganisms.

EXAMPLE I

Bacterial strain: Staphylococcus aureus ATCC 6538
Concentration of the microorganism: 3.45.10⁶ germs per ml of water.

Ammonium quaternary polymer of example 10.

Destruction speed of bacterial germs.

| Amount and nature of the ingredients added to the water | Contact time (minutes) | % of remaining bacteria |
|---|---|---|
| 1 ppm copper ions | 1 | 100 |
| 40 ppb silver ions | 1 | 100 |
| 3 ppm of polymer of example 10 | 1 | 1.45 |
| 1 ppm copper ions + 40 ppb silver ions + 3 ppm of polymer of example 10 | 1 | 0.003 |

EXAMPLE II

Bacterial strain: Escherichia coli ATCC 11229
Initial concentration of the bacterial germs: $21.10^4$ germs per ml
Ammonium polymer of example 10.

Destruction speed of bacterial germs

| Amount and nature of the ingredients added to the water | Contact time (minutes) | % of remaining bacteria |
|---|---|---|
| 3 ppm polymer of example 10 | 5 | 3 |
| 1 ppm copper ions | 5 | ~100 |
| 40 ppb silver ions | 5 | ~100 |
| 3 ppm polymer of example 10 + 1 ppm copper ion + 40 ppb silver ions | 5 | 0.009 |

EXAMPLE III

Bacterial strain: Pseudomonas aeruginosa ATCC 17934
Initial concentration of germs: $0.92.10^6$ germs per ml
Ammonium quaternary polymer of example 10.

Destruction speed of bacterial germs

| Amount and nature of the ingredients added to the water | Contact time (minutes) | % of remaining bacteria |
|---|---|---|
| 1 ppm polymer of example 10 | 5 | 48 |
| 1 ppm copper ions | 5 | ~100 |
| 5 ppb silver ions | 5 | ~100 |
| 1 ppm polymer of example 10 + 1 ppm copper ions + 5 ppb silver ions | 5 | 0.008 |

EXAMPLE IV

Bacterial strain: Streptococcus faecalis ATCC 6569
Concentration of bacterial germs: $1.16.10^6$ germs per ml
Ammonium quaternary polymer of example 10.

Destruction speed of bacterial germs

| Amount and nature of the ingredients added to the water | Contact time (minutes) | % of remaining bacteria |
|---|---|---|
| 3 ppm polymer of example 10 | 1 | 0.024 |
| 1 ppm copper ions | 1 | ~100 |
| 40 ppb silver ions | 1 | ~100 |
| 3 ppm polymer of example 10 + 1 ppm copper ions + 40 ppb silver ions | 1 | 0.0004 |

EXAMPLE V

Bacterial strain: Escherichia coli ATCC 11229
Concentration of bacterial germs: $10.8.10^4$ germs per ml
Ammonium quaternary polymer of example 10.

Destruction speed of bacterial germs

| Amount and nature of the ingredients added to the water | Contact time (minutes) | % of remaining bacteria |
|---|---|---|
| 3 ppm polymer of example 10 | 5 | 0.4 |
| 1 ppm copper ions | 5 | ±100 |
| 40 ppb silver ions | 5 | ±100 |
| 10 ppb silver ions | 5 | ±100 |
| 3 ppm polymer of example 10 + 1 ppm copper ions | 5 | 0.006 |
| 3 ppm polymer of example 10 + 10 ppb silver ions | 5 | 0.13 |
| 3 ppm polymer of example 10 + 40 ppb silver ions | 5 | 0.008 |
| 3 ppm polymer of example 10 + 1 ppm copper ions + 40 ppb silver ions | 5 | 0.0009 |

EXAMPLE VI

Bacterial strain: Escherichia coli ATCC 11229
Initial concentration of bacterial germs: $93.10^4$ germs per ml
Ammonium quaternary polymer of example 10.

Destruction speed of the bacterial germs

| Amount and nature of the ingredients added to the water | % of remaining bacteria after | | |
|---|---|---|---|
| | 30 seconds | 1 minute | 5 minutes |
| 1 ppm Cu | ~100 | ~100 | ~100 |
| 5 ppb Ag | ~100 | ~100 | ~100 |
| 5 ppm polymer of example 10 | 8.98 | 2.60 | 0.12 |
| 1 ppm Cu + 5 ppm polymer of example 10 | 2.41 | 1.11 | 0.11 |
| 1 ppm Cu + 20 ppb Ag + 5 ppm polymer of example 10 | 1.76 | 0.18 | 0.007 |

EXAMPLE VII

Bacterial strain: Escherichia coli ATCC 11229
Initial concentration of bacterial germs: $93.10^4$ germs per ml.
Ammonium polymer of example 6.

| Destruction speed of the bacterial germs | | |
|---|---|---|
| Amount and nature of the ingredients added to the water | % of remaining bacteria after | |
| | 1 minute | 5 minutes |
| 20 ppm of the polymer of example 6 | 22.58 | 1.41 |
| 20 ppm of the polymer of example 6 + 1 ppm Cu + 20 ppb Ag | 1.02 | 0.04 |

EXAMPLE VIII

Bacterial strain: Streptococcus faecalis ATCC 6569
Initial concentration of bacterial germs: $85.5 \cdot 10^4$ germs per ml
Ammonium polymer of example 2.

| Destruction speed of the bacterial germs | |
|---|---|
| Amount and nature of the ingredients added to the water | % of remaining bacteria after 1 minute |
| 1 ppm Cu | ~100 |
| 5 ppb Ag | ~100 |
| 10 ppm of the polymer of example 2 | 0.17 |
| 10 ppm of the polymer of example 2 + 1 ppm Cu + 5 ppb Ag | 0.03 |

EXAMPLE IX

Bacterial strain: Streptococcus faecalis ATCC 6569
Initial concentration of bacterial germs: $85.5 \cdot 10^4$ germs per ml
Ammonium polymer of example 3.

| Destruction speed of the bacterial germs | |
|---|---|
| Amount and nature of the ingredients added to the water | % remaining bacteria after 5 minutes |
| 1 ppm Cu | ~100 |
| 5 ppb Ag | ~100 |
| 10 ppm of the polymer of example 3 | 0.35 |
| 10 ppm of the polymer of example 3 + 1 ppm Cu + 5 ppb Ag | 0.0006 |

EXAMPLE X

Bacterial strain: Streptococcus faecalis ATCC 6569
Initial concentration of bacterial germs: $85.5 \cdot 10^4$ germs per ml
Ammonium polymer of example 7.

| Destruction speed of the bacterial germs | | |
|---|---|---|
| Amount and nature of the ingredients added to the water | % of remaining bacteria after | |
| | 1 minute | 5 minutes |
| 1 ppm Cu | ~100 | ~100 |
| 5 ppb Ag | ~100 | ~100 |
| 10 ppm of the polymer of example 7 | 0.068 | 0.007 |
| 10 ppm of the polymer of example 7 + 1 ppm Cu + 5 ppb Ag | 0.015 | 0.0003 |

EXAMPLE XI

Bacterial strain: Escherichia coli ATCC 11229
Initial concentration of bacterial germs: $1.2 \cdot 10^4$ germs per ml
Ammonium polymer of example 8.

| Destruction speed of the bacterial germs | | | |
|---|---|---|---|
| Amount and nature of the ingredients added to the water | % of remaining bacteria after | | |
| | 1 minute | 5 minutes | 15 minutes |
| 1 ppm Cu | ~100 | ~100 | ~100 |
| 20 ppb Ag | ~100 | ~100 | ~100 |
| 5 ppm of the polymer of example 8 | 37.83 | 4.76 | 1.31 |
| 5 ppm of the polymer of example 8 + 1 ppm Cu | 10.04 | 0.57 | 0.027 |
| 5 ppm of the polymer of example 8 + 1 ppm Cu + 20 ppb Ag | 5.02 | 0.05 | 0.002 |

EXAMPLE XII

Bacterial strain: Escherichia coli ATCC 11229
Initial concentration of bacterial germs: $1.25 \cdot 10^4$ germs per ml.
Ammonium polymer of example 1.

| Destruction speed of the bacterial germs | | | |
|---|---|---|---|
| Amount and nature of the ingredients added to the water | % of remaining bacteria after | | |
| | 1 minute | 5 minutes | 15 minutes |
| 1 ppm Cu | ~100 | ~100 | ~100 |
| 20 ppb Ag | ~100 | ~100 | ~95 |
| 5 ppm of the polymer of example 1 | 16.25 | 1.88 | 0.55 |
| 5 ppm of the polymer of example 1 + 1 ppm Cu | 3.21 | 0.45 | 0.18 |
| 5 ppm of the polymer of example 1 + 1 ppm Cu + 20 ppb Ag | 2.40 | 0.09 | 0.008 |

EXAMPLE XIII

Bacterial strain: Staphylococcus aureus ATCC 6538.
Initial concentration of bacterial germs: $40 \cdot 10^4$ germs per ml
Ammonium polymer of example 9.

| Destruction of the bacterial germs | |
|---|---|
| Amount and nature of the ingredients added to the water | % of remaining bacteria after 1 minute |
| 1 ppm Cu | ~100 |
| 5 ppb Ag | ~100 |
| 5 ppm of the polymer of example 9 | 3.1 |
| 5 ppm of the polymer of example 9 + 1 ppm Cu + 5 ppb Ag | 0.2 |

EXAMPLE XIV

Bacterial strain: Escherichia coli ATCC 11229
Initial concentration of bacterial germs: $79.5 \cdot 10^4$ germs per ml
Ammonium polymer of example 9.

| Destruction speed of the bacterial germs | |
|---|---|
| Amount and nature of the ingredients added to the water | % of remaining bacteria after 5 minutes |
| 1 ppm Cu | ~100 |
| 5 ppb Ag | ~100 |
| 5 ppm of the polymer of example 9 | 4.47 |
| 5 ppm of the polymer of example 9 + 1 ppm Cu + 5 ppb Ag | 0.48 |

EXAMPLE XV

Bacterial strain: Escherichia coli ATCC 11229
Initial concentration of bacterial germs: $98.10^4$ germs per ml
Ammonium polymer of examples 10 and 13.

| Destruction speed of the bacterial germs | | | |
|---|---|---|---|
| Amount and nature of the ingredients added to the water | % of remaining bacteria after | | |
| | 30 seconds | 1 minute | 5 minutes |
| 5 ppm of the polymer of example 10 + 1 ppm Cu + 5 ppb Ag | 0.99 | 0.11 | 0.002 |
| 5 ppm of the polymer of example 13 + 1 ppm Cu + 5 ppb Ag | 23.5 | 7.09 | 0.27 |

The polymer of example 10 differs only from that of example 13 by its polymerization degree.
The higher the polymerization degree, the higher the bactericidal action.

EXAMPLE XVI

Bacterial strain: Staphylococcus aureus ATCC 6538
Initial concentration of bacterial germs: $81.5.10^4$ germs per ml
Ammonium polymer of example 26.

| Destruction speed of the bacterial germs | |
|---|---|
| Amount and nature of the ingredients added to the water | % of remaining bacteria after 5 minutes |
| 1 ppm Cu | ~100 |
| 5 ppb Ag | ~100 |
| 10 ppm of the polymer of example 26 | 0.25 |
| 10 ppm of the polymer of example 26 + 1 ppm Cu + 5 ppb Ag | 0.048 |

EXAMPLE XVII

Bacterial strain: Staphylococcus aureus ATCC 6538
Initial concentration of bacterial germs: $81.5.10^4$ germs per ml
Ammonium copolymer of example 31.

| Destruction speed of the bacterial germs | |
|---|---|
| Amount and nature of the ingredients added to the water | % of remaining bacteria after 5 minutes |
| 1 ppm Cu | ~100 |
| 5 ppb Ag | ~100 |
| 10 ppm of the copolymer of example 31 | 0.103 |
| 10 ppm of the copolymer of example 31 + 1 ppm Cu + 5 ppb Ag | 0.01 |

EXAMPLE XVIII

Bacterial strain: Staphylococcus aureus ATCC 6538
Initial concentration of bacterial germs: $81.5.10^4$ germs per ml.
Ammonium copolymer of example 32.

| Destruction speed of the bacterial germs | |
|---|---|
| Amount and nature of the ingredients added to the water | % of remaining bacteria after 5 minutes |
| 1 ppm Cu | ~100 |
| 5 ppb Ag | ~100 |
| 10 ppm of the copolymer of example 32 | 1.6 |
| 10 ppm of the copolymer of example 32 + 1 ppm Cu + 5 ppb Ag | 0.1 |

EXAMPLE XIX

Bacterial strain: Staphylococcus aureus ATCC 6538
Initial concentration of bacterial germs: $81.5.10^4$ germs per ml
Ammonium polymer of the example 34.

| Destruction speed of the bacterial germs | |
|---|---|
| Amount and nature of the ingredients added to the water | % of remaining bacteria after 5 minutes |
| 1 ppm Cu | ~100 |
| 5 ppb Ag | ~100 |
| 10 ppm of the polymer of example 34 | 0.54 |
| 10 ppm of the polymer of example 34 + 1 ppm Cu + 5 ppb Ag | 0.067 |

EXAMPLE XX

Bacterial strain: Escherichia coli ATCC 11229
Initial concentration of bacterial germs: $81.5.10^4$ germs per ml
Ammonium polymer of example 25.

| Destruction speed of the bacterial germs | | |
|---|---|---|
| Amount and nature of the ingredients added to the water | % of remaining bacteria after | |
| | 1 minute | 5 minutes |
| 1 ppm Cu | ~100 | — |
| 5 ppb Ag | ~100 | — |
| 10 ppm of the polymer of example 25 | 4.6 | 0.85 |
| 10 ppm of the polymer of example 25 + 1 ppm Cu + 5 ppb Ag | 0.5 | 0.004 |

EXAMPLE XXI

Bacterial strain: Escherichia coli ATCC 11229
Initial concentration of bacterial germs: $81.5 \cdot 10^4$ germs per ml
Ammonium polymer of example 27.

| Amount and nature of the ingredients added to the water | Destruction speed of the bacterial germs % of remaining bacteria after | |
|---|---|---|
| | 1 minute | 5 minutes |
| 1 ppm Cu | ~100 | — |
| 5 ppb Ag | ~100 | — |
| 10 ppm of the polymer of example 27 | 3.36 | 0.18 |
| 10 ppm of the polymer of example 27 + 1 ppm Cu + 5 ppb Ag | 0.026 | 0.000 |

EXAMPLE XXII

Bacterial strain: Saccharomyces cerevisiae.
Initial concentration of bacterial germs: $12.6 \cdot 10^4$ germs per ml
Ammonium polymer of example 10.

| Amount and nature of the ingredients added to the water | Destruction speed of the bacterial germs % of remaining bacteria after | |
|---|---|---|
| | 1 minute | 5 minutes |
| 1 ppm Cu | ~100 | ~100 |
| 5 ppb Ag | ~100 | ~100 |
| 5 ppm of the polymer of example 10 | 15.20 | 1.31 |
| 5 ppm of the polymer of example 10 + 1 ppm Cu + 5 ppb Ag | 4.98 | 0.02 |

EXAMPLE XXIII

Bacterial strain: Candida albicans
Initial concentration of bacterial germs: $7.4 \cdot 10^4$ germs per ml
Ammonium polymer of example 10.

| Amount and nature of the ingredients added to the water | Destruction speed of the bacterial germs % of remaining bacteria after | |
|---|---|---|
| | 1 minute | 5 minutes |
| 1 ppm Cu | ~100 | ~100 |
| 10 ppb Ag | ~100 | ~100 |
| 10 ppm of the polymer of example 10 | 13.17 | 1.75 |
| 10 ppm of the polymer of example 10 + 1 ppm Cu + 10 ppb Ag | 4.12 | 0.09 |

EXAMPLE XXIV

Bacterial strain: Streptococcus faecalis ATCC 6569
Initial concentration of the bacterial germs: $115 \cdot 10^4$ germs per ml
Ammonium polymers of the example 24, 25 or 27.

| Amount and nature of the ingredients added to the water | Destruction speed of the bacterial germs % of remaining bacteria after | |
|---|---|---|
| | 1 minute | 5 minutes |
| 10 ppm of the polymer of example 24 | 0.37 | 0.03 |
| 10 ppm of the polymer of example 24 + 1 ppm Cu + 5 ppb Ag | 0.04 | 0.004 |
| 10 ppm of the polymer of example 25 | 0.23 | 0.078 |
| 10 ppm of the polymer of example 25 + 1 ppm Cu + 5 ppb Ag | 0.20 | 0.002 |
| 10 ppm of the polymer of example 27 | 0.86 | 0.15 |
| 10 ppm of the polymer of example 27 + 1 ppm Cu + 5 ppb Ag | 0.26 | 0.0001 |

EXAMPLE XXV

Treatment of a cutting oil used in the car industry containing various microorganisms by the ammonium polymer of example 10.

| Amount and nature of the ingredients added to the water | Destruction speed of the bacterial germs % of remaining bacteria after | |
|---|---|---|
| | 15 minutes | 1 heure |
| 1000 ppm of the polymer of example 10 + 10 ppm Cu | 5.4 | 0.00 |
| 1000 ppm of the polymer of example 10 + 10 ppm Mn | 2.5 | 0.05 |

EXAMPLE XXVI

Treatment of a cutting oil used in the car industry containing various micro-organisms with the ammonium polymer of example 24.

| Amount and nature of the ingredients added to the water | Destruction speed of the bacterial germs % of remaining bacteria after | |
|---|---|---|
| | 15 minutes | 1 heure |
| 1000 ppm of the polymer of example 24 + 10 ppm Cu | 0.05 | 0.00 |
| 1000 ppm of the polymer of example 24 + 10 ppm Mn | 0.54 | 0.05 |

EXAMPLE XXVII

Bacterial strain: Saccharomyces cerevisiae
Initial concentration of bacterial germs: $4.3 \cdot 10^4$ germs per ml
Treatment of a suspension of Saccharomyces cerevisiae simultaneously with the ammonium polymer of example 10, copper and silver ions and a non ionic surfactant (such as polyoxyethylene fatty alcohol).

| Destruction speed of bacterial germs | | |
| --- | --- | --- |
| Amount and nature of the ingredients added to the water. | % of remaining bacteria after | |
| | 1 minute | 5 minutes |
| 10 ppm of the polymer of example 10 + 1 ppm Cu + 5 ppb Ag | 0.020 | 0.000 |
| 10 ppm of the polymer of example 10 + 250 ppm of surfactant + 1 ppm Cu + 5 ppb Ag | 0.010 | 0.000 |

EXAMPLE XXVIII

Treatment of a suspension of Lactobacillus Bulgaris taken from the serum floating on the surface of a yoghurt, with the ammonium polymer of example 10 in the presence of copper and/or manganese ions.

| Destruction speed of the bacterial germs | | |
| --- | --- | --- |
| Amount and nature of the ingredients added to the water | % of remaining bacteria after | |
| | 1 minute | 5 minutes |
| 10 ppm of the polymer of example 10 + 1 ppm Cu | 11.1 | 0.53 |
| 10 ppm of the polymer of example 10 + 1 ppm Mn | 4.96 | 0.84 |
| 10 ppm of the polymer of example 10 + 1 ppm Mn + 1 ppm Cu | 4.27 | 0.47 |

What is claimed is:

1. A process for disinfection of aqueous liquids or infected surfaces, comprising treating said aqueous liquids or infected surfaces with an effective disinfecting amount of (a) at least one ion selected from the group consisting of copper, silver and manganese and (b) at least one quaternary ammonium polymer or copolymer, said polymer or copolymer being a condensation product obtained by condensation of at least one difunctional tertiary amine of the formula I

(I)

and at least one organic dihalide of the formula (IV)

X—B—X  (IV)

in which formulae:
R, A, B and X have the following means:
R designates a lower alkyl radical or the radical —CH$_2$—CH$_2$—OH;
X designates a halogen atom, and
A and B, which may be identical or different, with the proviso that the sum of the carbon atoms contained in A and B is greater than 8, and A and B have one of the five following formulae:

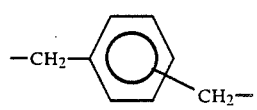
(1)

in which one of the substituents —CH$_2$— may be in an ortho, metha or para position,

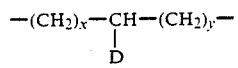
(2)

where D designates hydrogen or an alkyl radical containing less than four carbon atoms, and x and y are integers lower than 5, one of which may have a value equal to 0, while the sum x+y is at least equal to 1 and at most equal to 10, the radical (2) containing at most two double bonds,

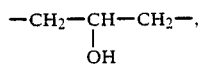
(3)

(4) —(CH$_2$)$_n$—O—(CH$_2$)$_n$—in which n is equal to 2 or 3, and

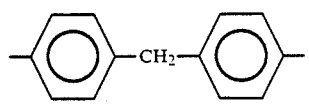
(5)

2. Process according to claim 1, in which copper ions are used in a proportion of 0.5 to 5 ppm of the aqueous liquid to be disinfected.

3. Process according to claim 1, in which silvers ions are used in a proportion of 1 to 50 ppb of the aqueous liquid to be disinfected.

4. Process according to claim 1, in which said at least one ion is supplied by electrolysis or by addition to the aqueous liquid of a water-soluble salt of said at least one ion.

5. Process according to claim 1, in which said halogen atom represented by X is a chlorine atom or a bromine atom.

6. Process according to claim 1, in which said polymer or copolymer condensation product is of the following formula (V)

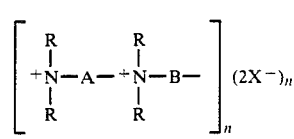
(V)

in which R, A, B and X have the above meanings, while n designates the degree of polymerization.

7. Process according to claim 6, in which the sum of the carbon atoms contained in A and B in the polymer or copolymer of formula V is equal to 9 to 10.

8. Process according to claim 6, in which at least one ammonium quaternary polymer of formula V as well as at least one water-soluble compound which is able to release ions of said at least one ion are used.

9. Process according to claim 6, in which the polymer or copolymer is a polymer of formula V, in which:
R=CH$_3$; A=(CH$_2$)$_6$,
B=CH$_2$—CH$_2$—CH$_2$, and
X=Br.

10. Process according to claim 9 in which said polymer of formula V is:
R=CH$_3$; A=(CH$_2$)$_6$,
B=—CH$_2$—CH$_2$—CH$_2$,
X=Br, and
n is equal to 28.

* * * * *

UNITED STATES PATENT AND TRADEMARK OFFICE
CERTIFICATE OF CORRECTION

PATENT NO. : 4,923,619

DATED : May 8, 1990

INVENTOR(S) : Alain C.A.G. Legros

It is certified that error appears in the above-identified patent and that said Letters Patent is hereby corrected as shown below:

ON THE TITLE PAGE:

In Item [73], please change assignee's address from "Nalinnes, Belgium" to read --Brussels, Belgium--.

Signed and Sealed this

Thirtieth Day of June, 1992

Attest:

DOUGLAS B. COMER

*Attesting Officer*    *Acting Commissioner of Patents and Trademarks*